(12) United States Patent
Sherwood

(10) Patent No.: US 8,229,554 B2
(45) Date of Patent: Jul. 24, 2012

(54) METHOD AND APPARATUS FOR SOLID STATE PULSE THERAPY CAPACITOR

(75) Inventor: Gregory J. Sherwood, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/178,285

(22) Filed: Jul. 7, 2011

(65) Prior Publication Data

US 2011/0270336 A1    Nov. 3, 2011

Related U.S. Application Data

(62) Division of application No. 11/858,034, filed on Sep. 19, 2007, now Pat. No. 7,979,120.

(60) Provisional application No. 60/871,372, filed on Dec. 21, 2006.

(51) Int. Cl.
*A61N 1/00* (2006.01)

(52) U.S. Cl. .................. 607/2; 607/4; 607/5; 361/311; 361/312; 361/313

(58) Field of Classification Search .................. 607/2
See application file for complete search history.

(56) References Cited

U.S. PATENT DOCUMENTS

| | | | |
|---|---|---|---|
| 3,914,666 A | 10/1975 | Schmickl et al. | |
| 4,510,935 A | 4/1985 | Spencer | |
| 5,416,042 A | 5/1995 | Beach et al. | |
| 5,461,536 A | 10/1995 | Beach et al. | |
| 5,545,184 A * | 8/1996 | Dougherty | 607/5 |
| 5,749,911 A | 5/1998 | Westlund | |
| 5,814,090 A | 9/1998 | Latterell et al. | |
| 6,006,133 A * | 12/1999 | Lessar et al. | 607/5 |
| 6,567,259 B2 | 5/2003 | Stevenson et al. | |
| 6,658,296 B1 | 12/2003 | Wong et al. | |
| 6,700,145 B1 | 3/2004 | Black et al. | |
| 6,730,559 B2 | 5/2004 | Agarwal et al. | |
| 6,819,544 B1 | 11/2004 | Nielsen et al. | |
| 6,836,683 B2 * | 12/2004 | Nielsen et al. | 607/36 |
| 6,888,188 B2 | 5/2005 | Basceri | |
| 6,891,217 B1 | 5/2005 | Agarwal et al. | |
| 7,033,406 B2 | 4/2006 | Weir et al. | |
| 7,259,443 B2 | 8/2007 | Blanchet-Fincher et al. | |
| 7,294,598 B2 | 11/2007 | Brize et al. | |

(Continued)

FOREIGN PATENT DOCUMENTS

EP    1676814 A1    7/2006

(Continued)

OTHER PUBLICATIONS

"U.S. Appl. No. 11/858,034, Notice of Allowance mailed Mar. 2, 2011", 11 pgs.
"Capacitors and the Implantable Defibrillator Market", *Feature, Passive Component Industry*, (Sep./Oct. 2001), 7-10.
"European Application Serial No. 10160749.7, European Search Report mailed Sep. 7, 2010", 3 pgs.

(Continued)

*Primary Examiner* — Carl H Layno
*Assistant Examiner* — Allen Porter, Jr.
(74) *Attorney, Agent, or Firm* — Schwegman, Lundberg & Woessner, P.A.

(57) ABSTRACT

One embodiment includes an apparatus that includes an implantable device housing, a capacitor disposed in the implantable device housing, the capacitor including a dielectric comprising $CaCu_3Ti_4O_{12}$ and $BaTiO_3$, the dielectric insulating an anode from a cathode and pulse control electronics disposed in the implantable device housing and connected to the capacitor.

20 Claims, 6 Drawing Sheets

U.S. PATENT DOCUMENTS

| | | |
|---|---|---|
| 7,342,755 B1 | 3/2008 | Horvat et al. |
| 7,408,187 B2 | 8/2008 | Kim et al. |
| 7,428,137 B2 | 9/2008 | Dowgiallo, Jr. |
| 7,466,536 B1 | 12/2008 | Weir et al. |
| 7,979,120 B2 | 7/2011 | Sherwood |
| 2003/0040779 A1 | 2/2003 | Engmark et al. |
| 2004/0127345 A1* | 7/2004 | Li et al. ............ 501/136 |
| 2004/0174658 A1 | 9/2004 | O'Phelan et al. |
| 2004/0240149 A1 | 12/2004 | Lessner et al. |
| 2005/0002147 A1 | 1/2005 | Nielsen et al. |
| 2005/0219788 A1 | 10/2005 | Chow et al. |
| 2006/0120020 A1* | 6/2006 | Dowgiallo, Jr. ............ 361/313 |
| 2008/0154320 A1 | 6/2008 | Sherwood |

FOREIGN PATENT DOCUMENTS

| | | |
|---|---|---|
| JP | 2002519844 A | 7/2002 |
| JP | 2003533019 A | 11/2003 |
| JP | 2006121087 A | 5/2006 |
| JP | 2006169011 A | 6/2006 |
| WO | WO-0184572 A2 | 11/2001 |
| WO | WO-2005114685 A1 | 12/2005 |
| WO | WO-2008076159 A1 | 6/2008 |

OTHER PUBLICATIONS

"European Application Serial No. 10160749.7, Office Action mailed Sep. 20, 2010", 6 pgs.

"European Application Serial No. 10160749.7, Response filed Mar. 18, 2011 to Non-Final Office Action mailed Sep. 20, 2010", 24 pgs.

"International Application Serial No. PCT/US2007/020292, International Search Report mailed Feb. 19, 2008", 5 pgs.

"International Application Serial No. PCT/US2007/020292, Written Opinion mailed Feb. 19, 2008", 7 pgs.

Fechine, P., et al., "Dielectric relaxation of BaTiO3 (BTO)-CaCu3Ti4O12 (CCTO) composite screen-printed thick films at low temperatures", Materials Chemistry and Physics, vol. 96, (2006), 402-408.

Kim, Il-Doo, et al., "Direct current bias effects on grain boundary schottky barriers", Applied Physics Letters, vol. 88 (072902), (2006), 1-3.

"Japanese Application Serial No. 2009-542757, Office Action mailed Oct. 11, 2011", 4 pgs.

* cited by examiner

METHOD AND APPARATUS FOR SOLID STATE PULSE THERAPY CAPACITOR

RELATED APPLICATION

This application is a Division of U.S. application Ser. No. 11/858,034, filed Sep. 19, 2007, now issued as U.S. Pat. No. 7,979,120, which claims the benefit of U.S. Provisional Application Ser. No. 60/871,372, filed Dec. 21, 2006, and which are hereby incorporated by reference in their entirety.

TECHNICAL FIELD

This disclosure relates generally to capacitors, and more particularly to a capacitor including a solid state design.

BACKGROUND

Implantable devices are used to provide pulses to a user. Cardiac rhythm management devices are among these. There are several ongoing needs which pressure designers to improve capacitors used in implantable devices.

Smaller size is needed. Smaller devices are easier to implant and are less invasive. Smaller devices can result from smaller capacitors. The energy storage capacity of capacitors is limited, in part, by size constraints of the device and the strength of the dielectric which separates one or more anode and cathode layers. Improved dielectric strength can increase performance and/or decrease size of a capacitor. Simplified construction is desired. Current electrolytic capacitors require features to safely enclose electrolyte and electrodes in a housing. Improved designs could reduce the need for some of these features. Elimination or reduction of reformation processes is also desired. Reformation requires energy, and shortens the service life of a device.

Overall, capacitors could be improved if they could answer one or more of these needs. Any changes to existing designs should be compatible with cost effective and efficient manufacturing processes.

SUMMARY

In an embodiment of the present subject matter, an apparatus includes an implantable device housing, a capacitor disposed in the implantable device housing, the capacitor including a dielectric comprising $CaCu_3Ti_4O_{12}$, the dielectric insulating an anode from a cathode, and pulse control electronics disposed in the implantable device housing and connected to the capacitor. In an embodiment, the capacitor has a volume of approximately 2.0 cubic centimeters. In an embodiment, the capacitor is adapted to store approximately 41 joules at approximately 800 volts.

In another embodiment, an apparatus includes an implantable device housing and a capacitor disposed in the implantable device housing. The capacitor includes a dielectric comprising $CaCu_3Ti_4O_{12}$ and $BaTiO_3$. The dielectric insulates an anode from a cathode. The apparatus also includes pulse control electronics disposed in the implantable device housing and connected to the capacitor. In an embodiment, the capacitor has a volume of approximately 2.0 cubic centimeters. In an embodiment, the capacitor is adapted to store approximately 41 joules at approximately 800 volts.

An example method includes insulating an anode of a capacitor and a cathode of the capacitor with a dielectric comprising $CaCu_3Ti_4O_{12}$, disposing the capacitor in an implantable device housing, disposing pulse control electronics in the implantable device housing, and connecting the capacitor to a stimulation electrode and to the pulse control electronics. The pulse control electronics switch the capacitor between an energy storage mode which stores a charge in the capacitor, and an energy delivery mode, which conducts the charge to the stimulation electrode. In an example, the capacitor is formed by a process including, forming a first dielectric layer comprising $CaCu_3Ti_4O_{12}$, forming a first electrode layer onto the first dielectric layer, forming a second dielectric layer comprising $CaCu_3Ti_4O_{12}$ on the first electrode layer, forming a second electrode layer onto the second dielectric layer, forming a third dielectric layer comprising $CaCu_3Ti_4O_{12}$ onto the second electrode layer, and connecting the first and second electrode layers to the pulse control electronics.

Another example method includes insulating an anode of a capacitor and a cathode of the capacitor with a dielectric comprising $CaCu_3Ti_4O_{12}$ and $BaTiO_3$, disposing the capacitor in an implantable device housing, disposing pulse control electronics in the implantable device housing, and connecting the capacitor to a stimulation electrode and to the pulse control electronics. The pulse control electronics switch the capacitor between an energy storage mode which stores a charge in the capacitor, and an energy delivery mode, which conducts the charge to the stimulation electrode. In an example, the capacitor is formed by a process including, forming a first dielectric layer comprising $CaCu_3Ti_4O_{12}$ and $BaTiO_3$, forming a first electrode layer onto the first dielectric layer, forming a second dielectric layer comprising $CaCu_3Ti_4O_{12}$ and $BaTiO_3$ on the first electrode layer, forming a second electrode layer onto the second dielectric layer, forming a third dielectric layer comprising $CaCu_3Ti_4O_{12}$ and $BaTiO_3$ onto the second electrode layer; and connecting the first and second electrode layers to the pulse control electronics.

One embodiment of the present subject matter includes an implantable apparatus for delivery of an energy pulse. The embodiment includes a biocompatible device housing. The embodiment additionally includes a monolithic capacitor disposed in the biocompatible device housing, the monolithic capacitor including an anode and a cathode, with a pervoskite dielectric separating the anode from the cathode. The embodiment also includes pulse control electronics disposed in the implantable device housing and connected the monolithic capacitor.

One embodiment of the present subject matter includes an implantable apparatus for delivery of an energy pulse. The embodiment includes an implantable device housing. The embodiment includes a capacitor disposed in the implantable device housing. The capacitor includes a plurality of planar anode and cathode layers, in the embodiment. The embodiment includes a pervoskite dielectric insulating at least one planar anode layer having an anode perimeter from at least one planar cathode layer having a cathode perimeter which is substantially coextensive with the anode perimeter. The embodiment includes pulse control electronics disposed in the implantable device housing and connected the capacitor, the pulse control electronics connected to the capacitor and adapted to discharge energy stored in the capacitor to generate the energy pulse. Of the implantable device housings disclosed in various embodiments herein, some are biocompatible.

Another embodiment of the present subject matter includes an implantable device housing, and a capacitor disposed in the implantable device housing. In the embodiment, the capacitor includes a $CaCu_3Ti_4O_{12}$ dielectric insulating an anode from a cathode. Pulse control electronics are disposed in the implantable device housing and connected to the capacitor, in the embodiment.

Another embodiment includes insulating an anode of a capacitor and a cathode of the capacitor with a pervoskite dielectric and disposing the capacitor in an implantable device housing such that the pervoskite dielectric is not coupled to the implantable device housing. The embodiment includes disposing pulse control electronics in the implantable device housing and connecting the capacitor to a stimulation electrode and to the pulse control electronics, where the pulse control electronics switch the capacitor between an energy storage mode which stores a charge in the capacitor, and an energy delivery mode, which conducts the charge to the stimulation electrode.

Another embodiment includes insulating an anode of a capacitor and a cathode of the capacitor with a pervoskite dielectric, disposing the capacitor in an implantable device housing such that the pervoskite dielectric is exposed to an interior surface of the implantable device housing, disposing pulse control electronics in the implantable device housing and connecting the capacitor to a stimulation electrode and to the pulse control electronics, where the pulse control electronics switch the capacitor between an energy storage mode which stores a charge in the capacitor, and an energy delivery mode, which conducts the charge to the stimulation electrode.

One embodiment includes an implantable device housing; pulse control electronics disposed in the implantable device housing and a capacitor means for storing a charge for a therapy pulse without transporting charge through electrolyte, the capacitor means being disposed in the implantable device housing and including dielectric means for isolating a cathode of the capacitor means from an anode of the capacitor means.

Various options are additionally discussed for use with one or more of the embodiment recited herein. Options include selecting a pervoskite which provides a dielectric constant falling in the range of around 2000 to around 30000. Embodiments optionally include a pervoskite dielectric including $CaCu_3Ti_4O_{12}$. Some embodiments optionally include a pervoskite including $BaTiO_3$. Embodiments are designed to operate at up to 800 volts. Multiple embodiments are included, some of which have a unique layer configuration. Embodiments are presented in which a capacitor of the present subject matter is used in a defibrillator. Pacemaker embodiments are also contemplated.

One embodiment of the present subject matter includes an implantable device housing. The embodiment includes a capacitor disposed in the implantable device housing, the capacitor including a pervoskite dielectric insulating an anode from a cathode. The embodiment includes an carrier connected to the capacitor and at least partially enveloping the capacitor. The embodiment includes pulse control electronics disposed in the implantable device housing and connected the capacitor, the pulse control electronics connecting the capacitor to at least one stimulation electrode, the pulse control electronics adapted to discharge a charge stored in the capacitor to the stimulation electrode.

Another embodiment of the present subject matter includes disposing a capacitor having an anode insulated from a cathode with a pervoskite dielectric into capacitor in a carrier. The embodiment includes disposing the carrier in an implantable device housing. The embodiment includes disposing pulse control electronics in the implantable device housing. The embodiment also includes connecting the capacitor to a stimulation electrode and to the pulse control electronics. In the embodiment, the pulse control electronics switch the capacitor between an energy storage mode which stores a charge in the capacitor, and an energy delivery mode, which conducts the charge to the stimulation electrode.

One embodiment of the present subject matter includes an implantable device housing. The embodiment includes pulse control electronics disposed in the implantable device housing. The embodiment additionally includes capacitor means for storing a charge for a therapy pulse without transporting charge through electrolyte, the capacitor means being disposed in the implantable device housing and including dielectric means for isolating a cathode of the capacitor means from an anode of the capacitor means. The embodiment includes carrier means for fixing the location of the capacitor in the implantable device housing.

Various options are additionally discussed for use with one or more of the embodiment recited herein. Options include selecting a pervoskite which provides a dielectric constant falling in the range of around 2000 to around 30000. Embodiments optionally include a pervoskite dielectric including $CaCu_3Ti_4O_{12}$. Some embodiments optionally include a pervoskite including $BaTiO_3$. Embodiments are designed to operate at up to 800 volts. Multiple embodiments are included, some of which have a unique layer configuration. Embodiments are presented in which a capacitor of the present subject matter is used in a defibrillator. Pacemaker embodiments are also contemplated.

Embodiments are presented in which a capacitor of the present subject matter is used in an implantable defibrillator.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their legal equivalents.

DETAILED DESCRIPTION

Figure 1:
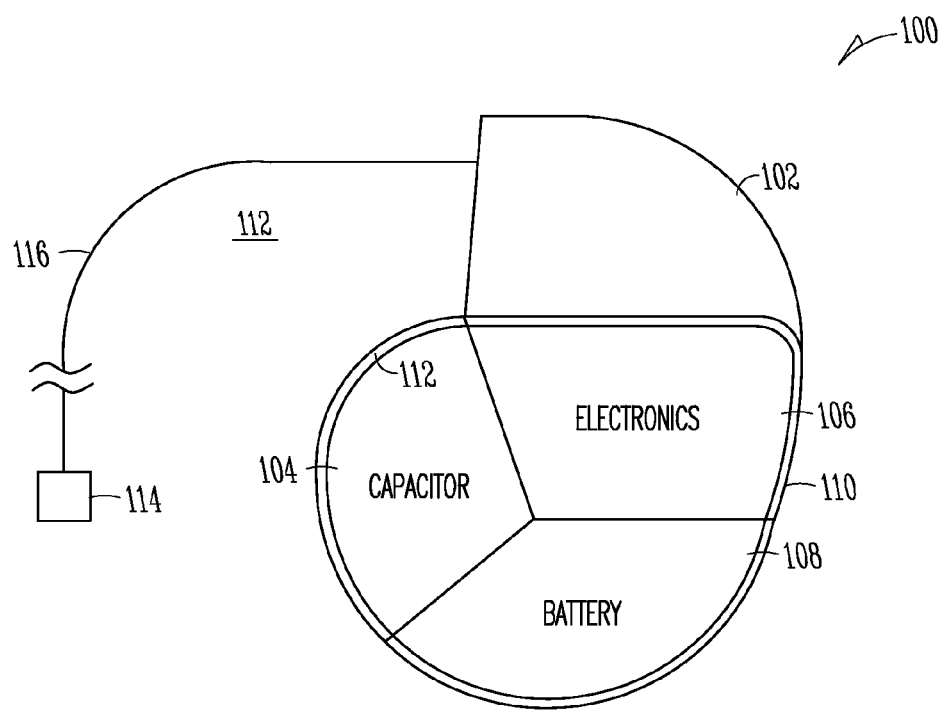
FIG. 1 shows an implantable device, according to one embodiment of the present subject matter.

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

The present subject matter relates to improved method and apparatus for a solid state capacitor. Capacitance is calculated by the following formula in equation 1.

$$C = \frac{kEA}{d} \quad (1)$$

In equation one, C relates to capacitance, k relates to a dielectric constant, E relates to the permittivity constant, A relates to the area of the electrodes, and d relates to the distance between electrodes. Equation one demonstrates that an increased capacitance can be achieved either by increasing the area of the electrodes (A), by decreasing the distance between electrodes (d), or by increasing the dielectric constant of the dielectric separating the electrodes (k). The present subject matter includes dielectrics which offer an increased dielectric constant and substantially linear charging characteristics. More specifically, the present subject matter concerns solid state capacitors.

Various methods are known for enhancing the dielectric constant of ceramic capacitors. Example methods are described, for example, in U.S. Pat. Nos. 5,808,856, 5,680,685, and 5,603,147, which are incorporated by reference herein in their entirety.

Various embodiments of the present subject matter include a ceramic capacitor that has substantially linear charging characteristics. In an implantable medical device that delivers a defibrillation electrostimulation therapy, it is important to be able to control the morphology of the therapeutic waveform delivered by the device. Selecting a capacitor with a substantially linear charging curve allows for better control over the morphology of the waveform of the electrostimulation therapy delivered by the device.

In an example, the implantable device includes a capacitor including a pervoskite dielectric that has substantially linear charging characteristics. Many dielectrics exhibit ferroelectric properties, i.e. they exhibit a nonlinear increase in voltage with a constant applied current. This nonlinearity represents saturation of the dielectric, which results in reduced incremental capacitance with increased voltage and nonlinear charging curve.

The present implantable medical device utilizes a dielectric with nonferroelectric properties. A nonferroelectric dielectric exhibits a substantially linear charging curve, i.e. a substantially constant increase in voltage over time with a constant applied current.

In an example implantable medical device, a capacitor is charged with a 16 mA constant current for 6 seconds with an initial voltage of 0V and a final voltage of about 800V. Substantially linear charging is achieved if the increase in voltage per second is substantially constant for all six second increments. For this example, this increment would be about 133V/second.

Some embodiments include a calcium copper titanium oxide dielectric (CCTO), which exhibits substantially linear charging characteristics. The chemical formula for CCTO is $CaCu_3Ti_4O_{12}$. Some CCTO capacitors have a dielectric constant (k) of at least 15,000-18,000.

Additional embodiments include a mixture of barium titanate ("BTO") and other components that provide substantially linear charging properties which BTO alone lacks. BTO has the chemical formula of $BaTiO_3$. Barium titanate alone has unacceptably non-linear charging characteristics. However, a mixture of BTO and another material such as CCTO can provide substantially linear charging characteristics. Thus, an example embodiment includes a ceramic capacitor formed from a mixture of barium titanate with CCTO.

FIG. 1 shows an implantable device 100, according to one embodiment of the present subject matter. Various embodiments of the present subject matter include an apparatus which includes an implantable device housing 110. Additionally, various embodiments include a capacitor 104 disposed in the implantable device housing 110. The capacitor 104 includes a pervoskite dielectric insulating the anode from the cathode, in various embodiments. It should be noted that the present subject matter is not limited to capacitors in which pervoskite is the sole dielectric insulator. Capacitors having dielectrics which are a combination of pervoskite and other materials are also contemplated. It should additionally be noted that the illustrated configuration of components and their orientation to one another is but one of the configurations contemplated by the present subject matter.

Various embodiments include a capacitor 104 which does not include a capacitor case. A capacitor case, in various embodiments, provides a physical shell which encases capacitor subcomponents. In various embodiments, the capacitor, as such, is a chip. In various embodiments, a pervoskite dielectric of capacitor 104 is at least partially open to an interior surface 112 of the implantable device housing 110. In some embodiments, capacitor electrodes are least partially open to an interior surface 112 of the implantable device housing. In various embodiments, at least some capacitor components are exposed to an interior surface 112.

Capacitors which are packaged in plastic are contemplated in various embodiments. Some embodiments include a capacitor which is at least partially encapsulated by an electrically insulative casing. In some of these embodiments, the insulative casing is exposed to interior surface 112. Some of these embodiments include a capacitor which is enclosed in a heat shrink film.

Various embodiments additionally include pulse control electronics 106 disposed in the implantable device housing 110 and connected the capacitor 104. In various embodiments, the pulse control electronics include cardioverter defibrillator electronics. In various embodiments, the pulse control electronics 106 are adapted to discharge a charge stored in the capacitor 104 to the stimulation electrode 114. In various embodiments, the charge is selected so as to be therapeutically effective. A therapeutically effective pulse to treat defibrillation is contemplated. Additionally, a therapeutically effective pulse to affect cardioversion is contemplated. Pulses which are therapeutically effective to pace the heart are contemplated. Pulses which are therapeutically effective to treat other diseases are additionally contemplated by the present subject matter.

The pulse control electronics 106 are connected to at least one stimulation electrode 114, in various embodiments. Additionally, some embodiments include a lead 116 which connects the electrode 114 to the pulse control electronics 106 and which is sealed to the implantable device housing 110.

In some embodiments, the implantable device housing is part of an electrode system. For example, embodiments having a metallic case can utilize such a case as part of either an anode electrode or a cathode electrode. The present subject matter contemplates device cases including, but not limited to, stainless steel, titanium, or combinations thereof. The present subject matter additionally includes metals not expressly listed herein.

Various embodiments of the present subject matter include a pervoskite dielectric which includes CCTO. Additional embodiments of the present subject matter include a pervoskite dielectric which includes CCTO combined with $BaTiO_3$. The following is one example of a process for producing a CCTO capacitor.

In the example process, CCTO ceramic pellets are prepared by a conventional solid-state reaction method. High purity $CaCO_3$ (99.99%), CuO (99.9%), and $TiO_2$ (99.99%) powders are ball milled for approximately 24 hours, and calcined at 900° C. for 11 hours. The powders are pressed into pellets. The pellets are sintered in a tube furnace at 1100° C. in air for 3 hours. Platinum electrodes are sputtered onto the pellet face. In some embodiments, the electrodes are 2 mm wide, 10 mm long and 2 mm apart. In one embodiment, AC impedance measurements were carried out between room temperature and 375° C. over the frequency range of 1 Hz-10 MHz with an applied AC voltage of 100 mV. In various embodiments, a DC bias between 0 and 5 V was applied between the electrodes to examine nonlinearity effects. In some embodiments, the impedance spectra were modeled using an equivalent circuit with two parallel RC elements, for the grain and grain boundary regions, connected in series. This model captures the relatively small bulk resistance in series with blocking grain boundary regions that give rise to the large DC (total) resistance of the polycrystalline CCTO ceramics. The observed spectra gives rise to a single distinct semicircle in the complex impedance plane offset from the origin allowing for the deconvolution of the respective R and C values.

Embodiments of the present subject matter demonstrate capacitors having an improved energy density. For example, some capacitors of the present subject matter have an energy density of about 20.5 joules per cubic centimeter of capacitor volume. Some embodiments include a capacitor which is adapted to store approximately 41 joules. Some embodiments store approximately 41 joules at approximately 800 volts.

Improved energy densities are possible due, in part, to dielectrics having an improved insulative ability. Embodiments of the present subject matter include capacitors having a dielectric constant of at least 2000. Some embodiments have a capacitor with a constant of approximately 3900. Additional embodiments have a dielectric constant of at least 15,000-18,000. The strength of the dielectric depends, in part, on the thickness of the dielectric. A thicker dielectric is useful in the storage of increased charge amounts. In various embodiments, a thick dielectric coating can be more susceptible to damage.

The dielectric constant is dependent, in part, on the frequency of a voltage applied to the capacitor. Various embodiments of the present subject matter subject the capacitor to a 120 Hz voltage. Additionally frequency values are possible.

Improved energy density allows for capacitors having a decreased size. The present subject matter allows for capacitors which have a volume of from above 0 cubic centimeters to about 4 cubic centimeters. Some capacitors of the present subject matter are approximately 2 cubic centimeters in volume.

Some capacitor embodiments of the present subject matter are able to store 41 joules of energy at 800 volts using a capacitor having a volume of approximately 2 cubic centimeters. Storing such energy levels at such voltages at such volumes was not possible in previous capacitor designs. Such designs save space, improving patient comfort and simplifying implantation procedures. Such designs are able to administer therapies currently known. Such designs make possible new designs which were previously hampered by requiring unacceptably large capacitors.

FIG. 1 shows one application for capacitors of the present subject matter. The present subject matter contemplates various implantable devices. The present subject matter extends to, but is not limited to, applications such as pacemakers, defibrillators, congestive heart failure devices, and/or combinations thereof. This list is not exhaustive or exclusive of the present subject matter, and additional applications using capacitors are contemplated. It should be noted that the subject matter is suitable for use in various applications which require a capacitor. These applications include implantable devices and devices which are not implanted.

Device 100 includes a lead system 116. In various embodiments, lead system 116 extends to a therapy site. In various embodiments, lead system 116 is sealed to housing 110. In some of these embodiments, a header 102 seals the lead system to the housing 110. In some embodiments of the present subject matter, a therapy site includes a patient's heart. In some of these embodiments, an electrode 114 is in contact with a patient's heart. Additional areas targeted for therapy are additionally contemplated.

Shown schematically are portions of monitor 100 including electronics 106. In various embodiments, electronics 106 are able to monitor patient activity. In additional embodiments, electronics 106 are able to coordinate the application of therapy to a patient. Embodiments which do no rely on electronics 106 to direct a power source to administer therapy also are contemplated by the present subject matter.

Various embodiments of the present subject matter include a power source. Some embodiments include a battery 108. Additional embodiments include a capacitor 104. Capacitors discussed herein are used with device 100, in various embodiments.

Figure 2:
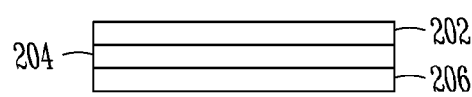
FIG. 2 shows electrodes in a solid state capacitor, according to one embodiment of the present subject matter.

FIG. 2 shows electrodes in a solid state capacitor, according to one embodiment of the present subject matter. The embodiment shows a first electrode 202, a second electrode 206, and a dielectric layer 204 disposed between the first electrode 202 and the second electrode 206. In some embodiments, the first electrode 202 is anodic. Some embodiments include a second electrode 206 which is cathodic. In various embodiments, the dielectric layer includes pervoskite exhibiting a substantially linear charging characteristic. This is a basic representation of how a dielectric separates one electrode from another. The present subject matter includes additional configurations, including those which are not depicted in this patent application expressly.

The illustrated embodiment shows a first electrode 202, a second electrode 206, and a dielectric layer 204 configured into a monolithic capacitor. In such a configuration, the anode and cathode are fixed in the same structure. The present subject matter is not limited to monolithic embodiments. Further, the present subject matter is not limited to embodiments demonstrating a single monolithic capacitor as some embodiments include multiple monolithic capacitors.

Various packaging options are contemplated by the present subject matter. Some embodiments encase a plurality of electrodes, and associated dielectric, in a package. Some package embodiments are electrically insulative. Some package embodiments are molded to the plurality of electrodes. Package embodiments include insulative polymers are contemplated.

Various interconnection designs, for connecting the plurality of electrodes to another capacitor component, or to another device component, are contemplated. The present subject matter includes, but is not limited to, metal traces, vias, and wire bonding. Additional interconnection features are also contemplated.

Figure 3:
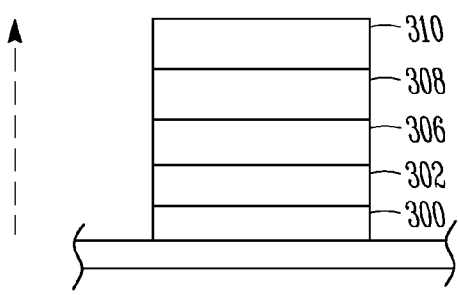
FIG. 3 shows capacitor electrodes of a solid state capacitor resting on a substrate, according to one embodiment of the present subject matter.

FIG. 3 shows capacitor electrodes of a solid state capacitor resting on a substrate, according to one embodiment of the present subject matter. Various embodiments include a capacitor in which a first pervoskite layer having a substantially linear charging characteristic 302 is disposed on a substrate 300. The capacitor includes a first electrode layer 304 disposed on the first pervoskite layer 302, in various embodiment. Various embodiments include a second pervoskite layer 306 disposed on the first electrode layer 304. Embodiments of the present subject matter include a second electrode 308 disposed on the second pervoskite layer 306. Some embodiments include a third pervoskite layer 310 disposed on the second conductive electrode 308. This layered arrangement is seen in some embodiments of the present subject matter. Additional embodiments include alternative arrangements. In various embodiments, the layers are layered 312 sequentially.

One embodiment of the present subject matter includes a first CCTO layer on a substrate. In the embodiment, a first electrode layer is disposed on the CCTO layer. A second CCTO layers is disposed on the first electrode layer in the embodiment. In the embodiment, a second conductive electrode is disposed on the second CCTO layer. The embodiment includes a third CCTO layer on the second conductive electrode. In some embodiments a mixture of BTO and CCTO is used to obtain a dielectric with a substantially linear charging characteristic.

The illustrated embodiment shows a first dielectric with a substantially linear charging characteristic, a first electrode, a second dielectric, a second electrode, and a third dielectric configured into a monolithic capacitor. In such a configuration, the anode and cathode are fixed in the same structure. The present subject matter is not limited to monolithic capacitor embodiments. Further, the present subject matter is not limited to embodiments demonstrating a single monolithic capacitor as some embodiments include multiple monolithic capacitors.

Figure 4:
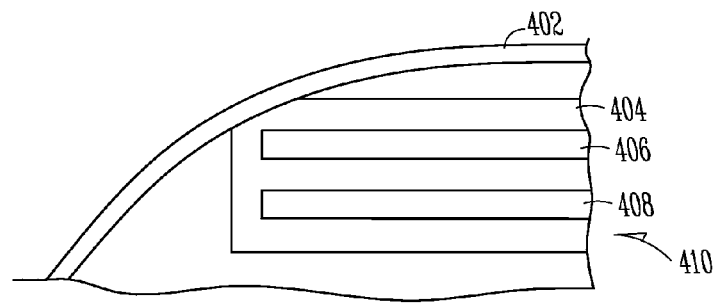
FIG. 4 shows a partial cross section of a solid state capacitor in a housing, according to one embodiment of the present subject matter.

FIG. 4 shows a partial cross section of a solid state capacitor in a housing, according to one embodiment of the present subject matter. The embodiment includes a housing 402 in which a capacitor 410 is disposed. The capacitor illustrated includes a pervoskite dielectric 404, a first electrode 406, and a second electrode 408. The embodiment illustrated includes a pervoskite dielectric which encases electrodes 406, 408. The illustration does not physically interconnect housing 402 to capacitor 410. In various embodiments, an abutment between housing 402 and capacitor 410 exists only so long as the capacitor 410 is held to the housing 402 with an external force. This is one embodiment of the present subject matter. Additional embodiments are also contemplated which feature different geometries, electrode configurations, dielectric configuration, and/or housing configurations.

Figure 5:
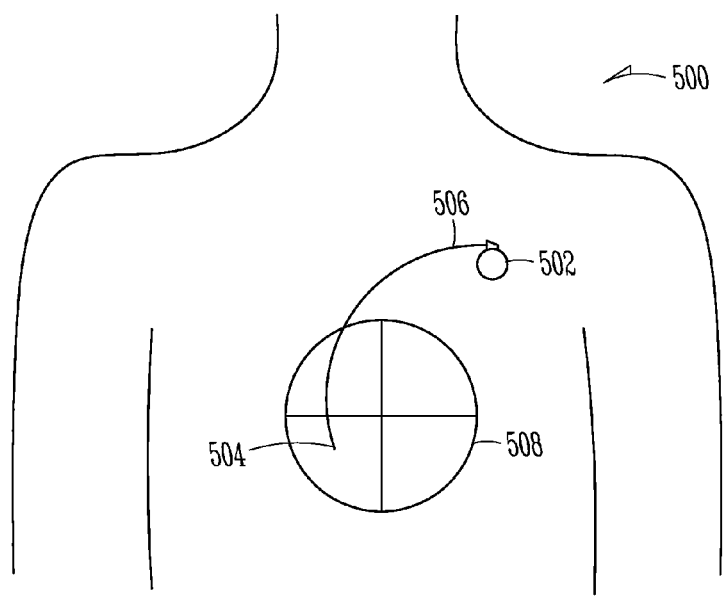
FIG. 5 shows a system including a solid state capacitor, with the system implanted in a patient, according to one embodiment of the present subject matter.

FIG. 5 shows a system including a solid state capacitor, with the system implanted in a patient, according to one embodiment of the present subject matter. The system 500 shows an implantable medical device 502 which includes a capacitor which has pervoskite dielectric features. The system 500 additionally includes an electrode 504. In various embodiments, a lead 506 extends between electrode 504 and implantable medical device 502. The electrode 504 is disposed in a heart 508, in various embodiments. Additional embodiments dispose an electrode in additional parts of a human anatomy. The present subject matter is not limited to a single electrode, as multiple electrode embodiments are compatible with the present subject matter. Various embodiments include a device housing of the implantable device 502 which is one of the electrodes needed to make an electrical circuit. In various embodiments, a housing electrode is paired with electrode 504 to define a therapy circuit. This is one system for energy delivery, and other systems, including those in which the housing is not an electrode, are contemplated by the present subject matter.

Figure 6:
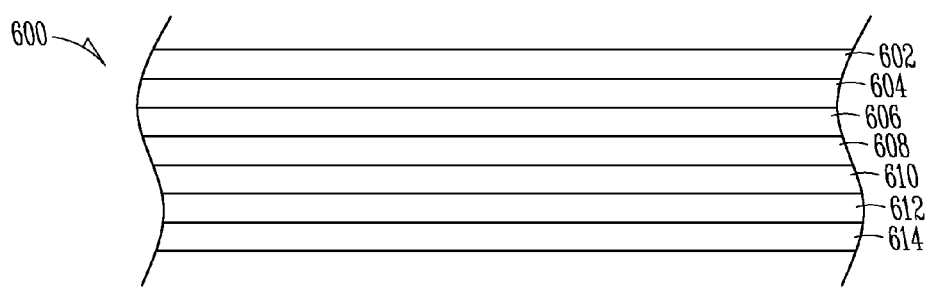
FIG. 6 shows electrode layers of a solid state capacitor, according to one embodiment of the present subject matter.

FIG. 6 shows electrode layers of a solid state capacitor, according to one embodiment of the present subject matter. The illustration includes a case 602, 614, in which a capacitor 600 is disposed. In various embodiments, the case 602, 614 is electrically connected with an anode of the electrode. In some embodiments, the case 602, 614 is anodic. In additional embodiments, the case 602, 614 is cathodic. In various embodiments, the capacitor includes a first pervoskite layer exhibiting a substantially linear charging characteristic 604, a first electrode 606, a second pervoskite layer 608, a second electrode 610, and a third pervoskite layer 612.

Various embodiments of the present subject matter include packaging configurations in which an implantable device housing 602, 614 houses a capacitor 600, without the need of an additional housing to house capacitor subcomponents. For example, the present subject matter does not require an electrolyte retaining housing. This is due, at least, to the insulative nature of the first 604 and third 612 pervoskite layers. In various embodiments, the first 604 and third 612 pervoskite layers are not coupled to the housing 602, 614. In additional embodiments, first 604 and third 612 pervoskite layers are coupled to the housing 602, 614. The illustrated cross section is a representative cross section of an implantable medical device for some embodiments of the present subject matter. It should be noted that the present subject matter includes embodiments in which the capacitor 600 does not abut housing 602, 614.

Figure 7:
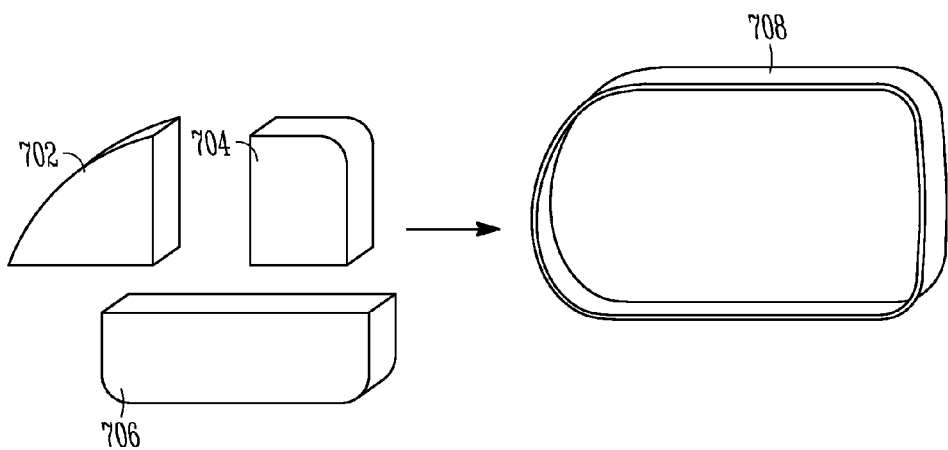
FIG. 7 is an exploded view of an implantable device, according to one embodiment of the present subject matter.

FIG. 7 is an exploded view of an implantable device, according to one embodiment of the present subject matter.

The pictured embodiment shows a capacitor 702 which has a form factor which is at least partially curved. Additionally pictured are electronics 704, and a battery 706. A case is pictured 708 that is adapted to receive the components 702, 704, 706. The form factor of the capacitor 702 and the other components 704, 706, enables packaging in the case while minimizing interstices which remain in the case after assembly. The curvature of the case 708, in various embodiments, is in accord with patient preferences, which are based in part on comfort. In some embodiments of the present subject matter, a capacitor 702 is curved along a surface which is orthogonal to a vector along which capacitor electrodes are layered. In various embodiments, a capacitor of the present subject matter exhibits a curved profile along a section face taken along a vector extending in the direction of layering. These are examples within the present subject matter, but are not exclusive of the present subject matter. The present subject matter additionally includes configurations in which a capacitor, battery, and additional components are layered onto one another.

Figure 8:
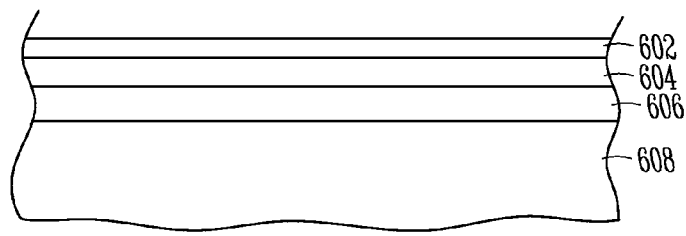
FIG. 8 is a partial cross section of a capacitor, according to one embodiment of the present subject matter.

FIG. 8 is a partial cross section of a capacitor, according to one embodiment of the present subject matter. In some embodiments of the present subject matter, a pervoskite coating 804 is physically connected to a capacitor casing 802. Some of these embodiments include a CCTO coating which is applied to the interior surface of a capacitor case 802 such that components packaged in the case 802 have a pervoskite layer disposed between the case 802 and the components 808. Also illustrated is a space 806 which is defined by the failure of components 808 and pervoskite lining 804 to touch. Such a space is optional, and does not exist in additional embodiments which are contemplated by the present subject matter.

Figure 9:
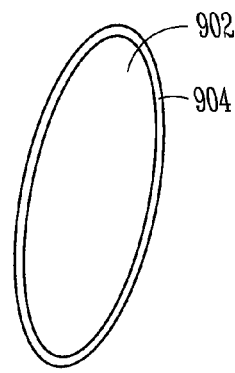
FIG. 9 is a top view of a capacitor connected to a carrier, according to one embodiment of the present subject matter.

FIG. 9 is a top view of a capacitor connected to a carrier, according to one embodiment of the present subject matter. Various embodiments of the present subject matter include a carrier 904 connected to the capacitor 902. In some embodiments, the carrier 904 at least partially envelopes the capacitor 902. In additional embodiments, the carrier 904 completely envelopes the capacitor 902. In these embodiments, the carrier 904 is configured to allow for electrical connection to the capacitor 902. Some examples include apertures in the carrier 904 through which capacitor terminals pass.

The carrier 904 is comprised of one or more materials. In various embodiments, the carrier 904 is electrically insulative. In some embodiments, the carrier 904 includes a resin which is at least partially cured. In some of these embodiments, the resins include a thermoset plastic. Plastics which are not thermoset are additionally contemplated by the present subject matter. A resin which includes epoxy is used in some embodiments.

In various embodiments, the carrier includes rubber. In some of these embodiments, the carrier includes a rubber piece elastically deformed around the capacitor. In some embodiments, a plurality of rubber pieces is connected to the capacitor and at least partially envelops the capacitor.

Figure 10:
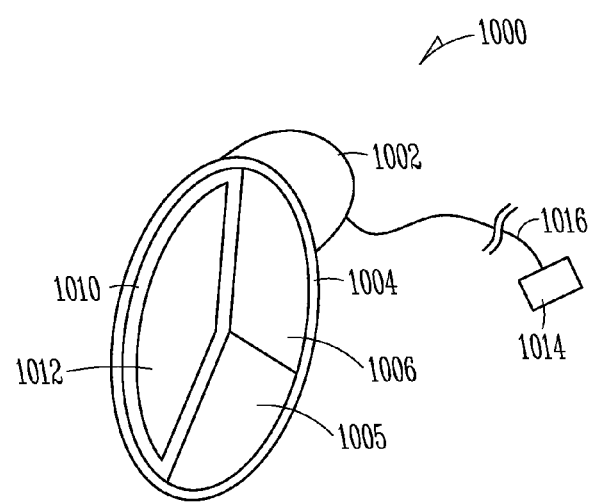
FIG. 10 shows an implantable medical device including a capacitor connected to a carrier, according to one embodiment of the present subject matter.

FIG. 10 shows an implantable medical device 1000 including a capacitor connected to a carrier, according to one embodiment of the present subject matter. Various embodiments include an implantable device housing 1004, a capacitor 1012 disposed in the implantable device housing 1004, the capacitor 1012 including a pervoskite dielectric insulating the anode from the cathode, and a carrier 1010. Various embodiments include a battery 1008.

In various embodiments, a carrier provides electrical insulation. In various embodiments, the carrier provides shock insulation. The carrier additionally serves to fix the location of a capacitor 1012 with respect to other components in an implantable medical device.

In various embodiments, pulse control electronics 1006 are disposed in the implantable device housing 1004 and connected the capacitor 1012. In various embodiments, the pulse control electronics 1006 connect the capacitor 1012 to at least one stimulation electrode 1014. In various embodiments, the pulse control electronics 1006 are adapted to discharge a charge stored in the capacitor to the stimulation electrode 1014. In some embodiments, the stimulation electrode 1014. In some embodiments, device housing 1004 is an electrode. In some embodiments, the device housing 1004 is not an electrode. In some embodiments, multiple electrodes are used. Some embodiments of the present subject matter use a lead 1016 to connect the stimulation electrode 1014 to a header 1002, which provides a sealed, conductive circuit to electronics disposed in the device housing 1004.

In various embodiments of the present subject matter, a capacitor 1012 is connected to a circuit board which functions as a carrier. In some of these embodiments, the circuit board is connected to the implantable device housing. In some of these embodiments, the circuit board substantially fixes the position of the capacitor with respect to the implantable device housing. In some of these embodiments, the circuit board is rigid and sized to abut the interior of housing 1004. In additional embodiments, a support structure is disposed in housing 1004 which fixes the location of one or more components inside the housing 1004. In some of these embodiments, a circuit board is connected to the support structure such that the circuit board's location is fixed with respect to the housing 1004.

Figure 11:
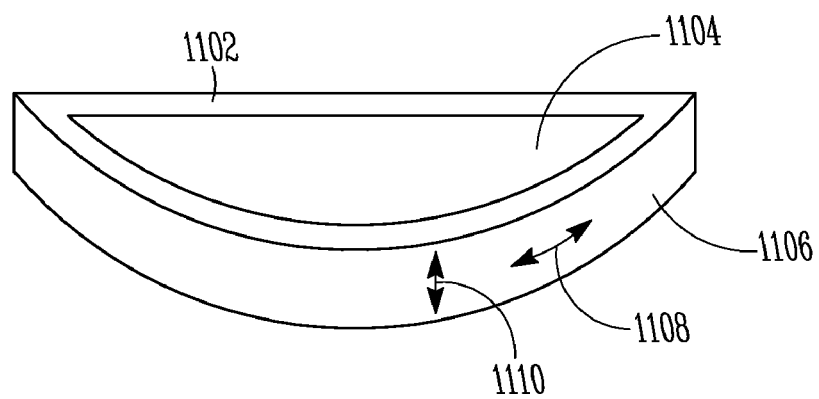
FIG. 11 is a perspective view of a capacitor connected to a carrier which extends along the capacitor edge, according to one embodiment of the present subject matter.

FIG. 11 is a perspective view of a capacitor connected to a carrier along a capacitor edge, according to one embodiment of the present subject matter. Although capacitor 1104 is D-shaped, in additional embodiments the capacitor is another shape, including, but not limited to, rectangular, circular, oval or other symmetrical or asymmetrical shapes.

In various embodiments, the carrier 1102 is a conformed film. In some embodiments, the carrier 1102 substantially envelops an edge face 1106 of capacitor 1104. Such perimeter film configurations are only some of the embodiments contemplated by the present subject matter. Other configurations exist in addition to those depicted herein expressly.

In various embodiments, conformable films, including the perimeter film 1102, are a heat shrink film. Additional embodiments include a thermoformed variety. Thermoformed embodiments use various materials, including polyvinyl chlorides (PVC), polyolefins, polysulfones, polyethersulfones, polyesters, polyetherimides, TEFLON and material using TEFLON, including PFAs, and PTFAs, polytetrafluoroethylenes (PTFE), polyimides, and polyethylene terephthalate glycols (PETG). TEFLON is a registered trademark of the E.I. DuPont de Nemours and Company Corporation, 101 West 10th St., Wilmington, Del. 19898. Various embodiments include parts formed at temperatures ranging from about 150 degrees centigrade to about 250 degrees centigrade. Time durations for forming thermoformed parts are variable depending on the shape of the part and the material requirements.

In some heat shrink film embodiments, the final conformed heat shrink film starts out as a ring shaped or tube shaped film. Some embodiments have a seam extending parallel along the axial length of the tube. Additional embodiments are seamless. Seamless varieties offer various advantages over seam embodiments, but are not widely available. Perimeter film 1102, in various embodiments, is conformed to a capacitor

1104. This involves fitting the perimeter film 1102 to the capacitor 1104, and then shrinking the perimeter film 1102 to the capacitor 1104, in various embodiments. In some embodiments, the tube walls substantially abut the edge 1106 of the capacitor 1104. The film is conformed to the capacitor such that the capacitor is bound, in various embodiments. Various heat shrink films are contemplated by the present subject matter. One heat shrink film comprises polyethylene terephthalate (PET). Various additional polymers include polyolefins, polyimides, MYLAR, PTFE, PVC, fluorinated ethylene propylene (FEP), perfluoroalkoxy (PFA), ethylene tetrafluoroethylene copolymer (ETFE), PETG, or combinations of these polymers. MYLAR is a registered trademark of the E.I. DuPont de Nemours and Company Corporation, 101 West 10th St., Wilmington, Del. 19898.

In various embodiments, film 1102 includes metal. Some of these embodiments include plastic laminated with a metal. Various embodiments of the present subject matter are useful for resisting laser light incident on the film 1102. Additionally, various embodiments of the present subject matter are useful for controlling electromagnetic interference. These benefits are not exclusive of exhaustive of the present subject matter.

In various examples, heat shrink film is colorless. Some colorless embodiments are substantially transparent. Substantially transparent heat shrink films are difficult to manage in processing and use, because they are hard to see. In some of these embodiments, a tint or coloring is added to the heat shrink film. A tint or coloring for a heat shrink film allows a user to see the film during handling and in use.

Conforming the film includes "heat shrinking", in various embodiments. Various examples of this process involve heating the plastic, once installed to a capacitor, with a heat source. Various embodiments use convection heat sources, but additional sources utilize heat radiation or combinations of heat radiation and convection. Various methods of heat shrinking are contemplated by the present subject matter. Some heat the heat shrink film with a heat source at a temperature ranging from about 150 degrees Centigrade to about 250 degrees Centigrade. The duration of heating ranges from about 10 seconds to about 10 minutes. In some embodiments, a cooling period of approximately 5 minutes is used to allow the material to stabilize before subjecting the capacitor 1104 to downstream processing steps.

Heat shrink films having various properties are contemplated by the present subject matter. Some heat shrink configurations are adapted to shrink at a first rate in a first direction, and to shrink at second rate in a second direction. In various embodiments, the material shrinks at a universal, consistent rate. In one embodiment, the material shrinks at or less than approximately a 3.7:1 ratio. In some embodiments, the material shrinks in a first direction 1108 from about 0 to about 3:1. In some of these embodiments, the material shrinks approximately 0 in a second direction 1110, orthogonal to the first direction. In some of these embodiments, if the second direction were greater than approximately zero, the perimeter would not envelope the edge 1106.

Heat shrink tubes or films of varying thicknesses are contemplated by the present subject matter. For example, tubes with a tube wall thickness of from about 0.0005 inches to about 0.002 inches are contemplated by the present subject matter. Tubes are fitted to capacitors in varying ratios of capacitor perimeter to tube circumference. Examples of tubes fitted to capacitors include to ratios of tube circumference to perimeter length of from about 0.95:1 to about 1.1:1. A parts combination with a 0.95:1 unshrunk tube volume to capacitor volume ratio requires some stretching of the heat shrink film before fitting it to the capacitor.

Various embodiments are electrically insulative. For example, in some embodiments, one or more conformed films are disposed between a capacitor and a conductive case, electrically insulating the capacitor from the conductive case.

Figure 12:
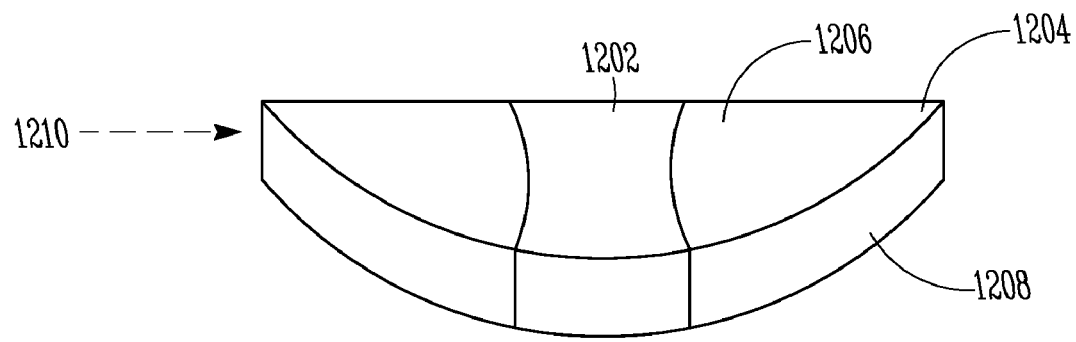
FIG. 12 is a perspective view of a capacitor which is banded by a carrier, according to one embodiment of the present subject matter.

FIG. 12 is a perspective view of a capacitor which is banded by a carrier, according to one embodiment of the present subject matter. Various embodiments include a band film 1202 encasing capacitor 1204. In various embodiments, the band film 1202 is a heat shrink film. In various embodiments, the conformed band film 1202 is banded around the capacitor 1204, with the band film 1202 crossing a top surface 1206 and a bottom surface opposing the top surface 1206. Band film 1202, in some embodiments, is tube shaped, and extends around the center of a capacitor orthogonal to the perimeter edge 1208 of the capacitor. In various embodiments, the band film 1202 is fitted 1210 over a capacitor 1204 while the band film 1202 is in an unconformed state, and is then is conformed to the capacitor 1204.

The illustrated band film 1202 has curvilinear aspects. In various embodiments, the film in an unconformed state does not present these aspects. The curvilinear aspects, in various embodiments, are a product of non-linear contraction rates of some heat shrink films. Various embodiments of the present subject matter are specially designed to compensate for these non-linear contraction rates. For example, in some embodiments, a band film which has yet to be conformed to a capacitor has a circumference ranging from about 95% of the size of the material to be enveloped to about 110% of the size of the material. In various embodiments, the width of the band film is from 0.25 inches to about 1.25 inches. The width is selected to ensure that a conformed band film 1202 is robust in capacitor processing and use.

In various embodiments, the band film is combined with other conformed films. For example, in some embodiments, a perimeter heat shrink film is combined with a band heat shrink film. Other configurations are possible as well. In some of these embodiments, all of the band films are shrunk at once using a heat shrink process. In additional embodiment, the films are conformed sequentially, using sequential heat shrink processes. These exact recitations are not intended to be limiting, and combinations of concurrent and sequential operations are possible without departing from the present subject matter.

Figure 13:
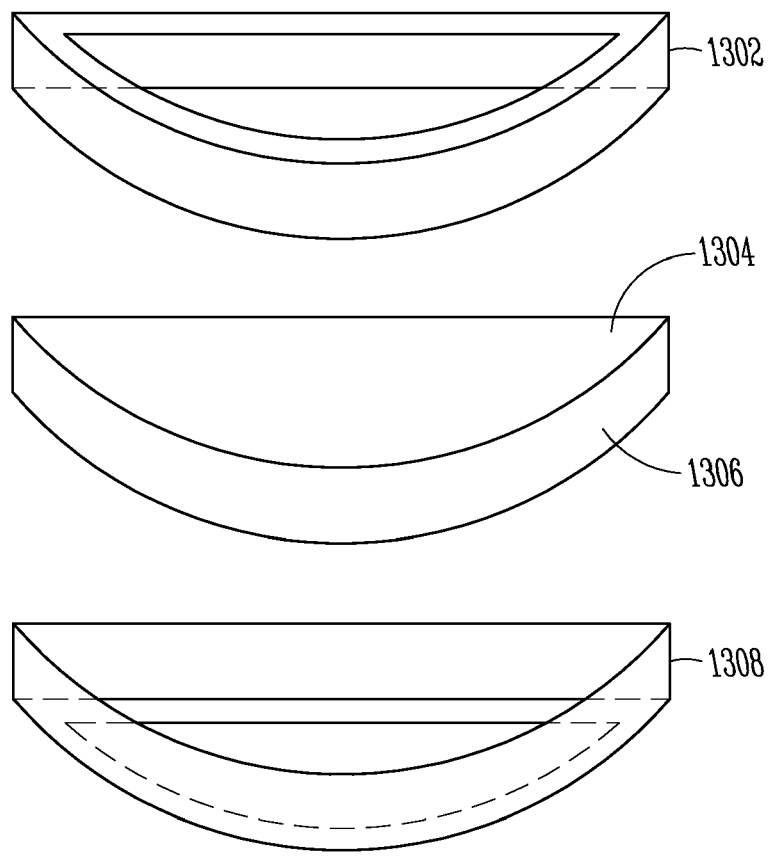
FIG. 13 is an exploded, perspective view of a capacitor and carrier components, according to one embodiment of the present subject matter.

FIG. 13 is an exploded, perspective view of a capacitor and associated components, according to one embodiment of the present subject matter. In various embodiments, a band film is disposed around a capacitor 1304 which is partially encapsulated by one or more preformed shells. Other embodiments combine a band film with a perimeter film which is conformed to the edge 1306 of capacitor 1304. In one embodiment, the preformed shells include a top portion 1302 and a bottom portion 1308. The illustrated preformed shells are of a heat shrink variety, but the present subject matter is not so limited. For example, thermoformed shells may be used. Some embodiments of preformed shells include conformed heat shrink films which are first shrunk to a mandrel, and then which are removed from the mandrel and applied to a capacitor.

Figure 14:
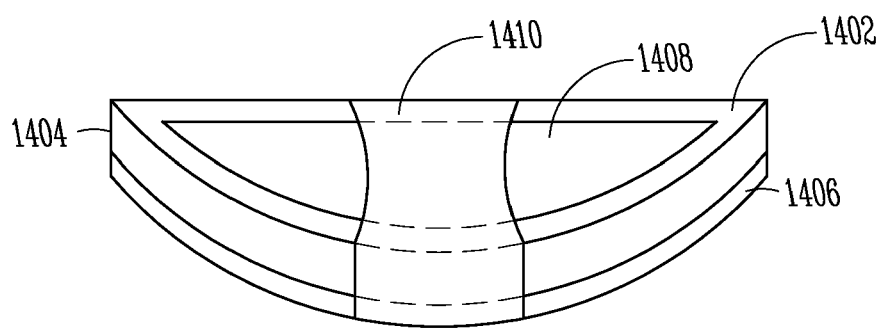
FIG. 14 is a perspective view of a capacitor connected to carrier components, according to one embodiment of the present subject matter.

FIG. 14 is a perspective view of a capacitor, according to one embodiment of the present subject matter. The illustration shows preformed shells 1402, 1406 which touch in a use position. In additional embodiments, preformed shells do not touch while in use. In one embodiment, the preformed films intersect in a use position with a lap joint 1404. But other configurations, such as a butt joint, are also possible.

The illustration additionally shows a band film 1410 which bands the capacitor 1408 and the preformed shells 1402, 1406. A perimeter film is additionally used in other embodiments. The configurations listed herein are not exhaustive or exclusive of the present subject matter, and additional embodiments are contemplated by the present subject matter.

Figure 15:
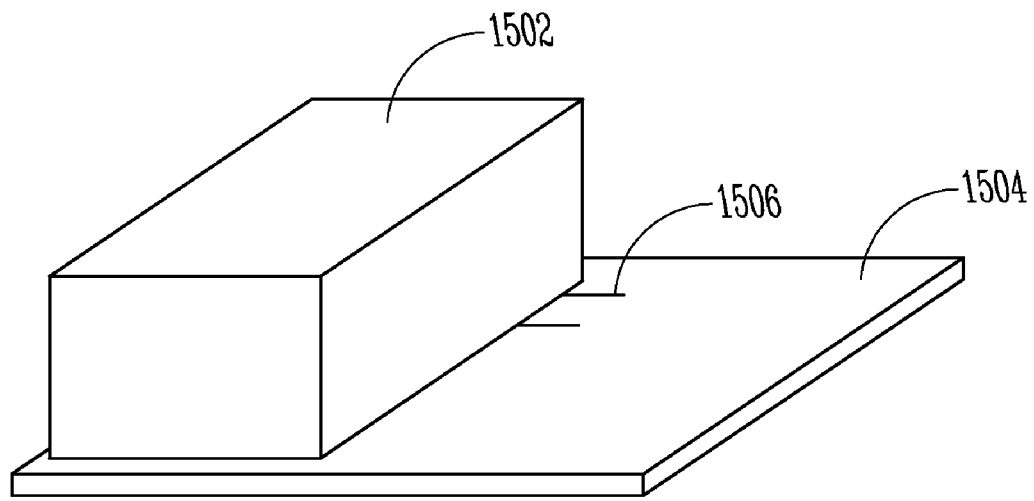
FIG. 15 is a perspective view of a capacitor connected to a substrate, according to one embodiment of the present subject matter.

FIG. 15 is a perspective view of a capacitor connected to a substrate, according to one embodiment of the present subject matter. In various embodiments, a carrier includes a substrate. In some embodiments, the substrate is a circuit board. In some of these embodiments, the capacitor is connected to circuits of the circuit board. In various embodiments, the circuit board includes fiberglass. In various embodiments, the circuit board includes flex circuitry. In various embodiments, the circuit board is a flex circuit board. In various embodiments, the carrier includes a socket connected to the circuit board. In some of these embodiments, the socket is plastic. In various embodiments, the circuit board includes through-hole features. Some circuit boards of the present subject matter include SMT mounting designs.

In various embodiments, terminals 1506 of capacitor 1502 are connected to a circuit board 1504. In additional embodiments, the capacitor 1502 includes caps and is mounted to the circuit board 1504 using an SMT design.

Figure 16:
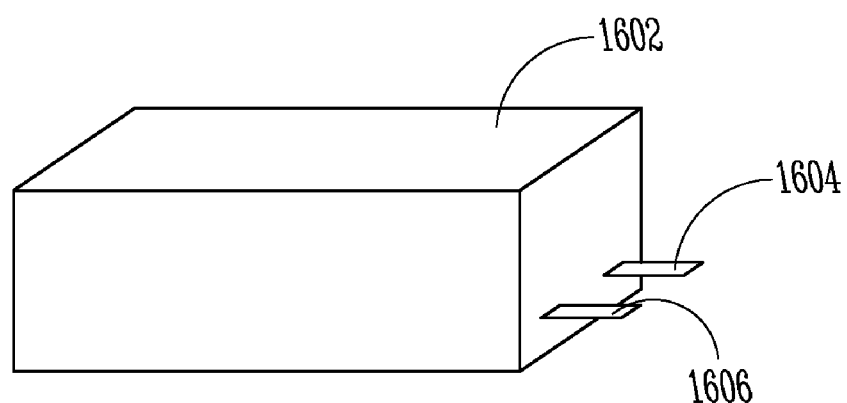
FIG. 16 is a perspective view of a capacitor having connection tabs, according to one embodiment of the present subject matter.

FIG. 16 is a perspective view of a capacitor having connection tabs, according to one embodiment of the present subject matter. In various embodiments, a circuit board to which a capacitor 1602 is mounted includes pads to which tabs 1604, 1606 of the capacitor 1602 are connected. In various embodiments, a first tab 1604 is connected to a capacitor anode of the capacitor and to a first pad. In various embodiments, a second tab is connected to a capacitor cathode of the capacitor and to a second pad.

Various embodiments of the present subject matter include a method which includes insulating an anode of a capacitor and a cathode of the capacitor with a pervoskite dielectric. In various embodiments, the method includes disposing the capacitor in a carrier. In some embodiments, the method includes disposing the carrier in an implantable device housing. Some embodiments use a method which includes disposing pulse control electronics in the implantable device housing. Various embodiments include connecting the capacitor to a stimulation electrode and to the pulse control electronics. Method embodiments are include wherein the pulse control electronics switch the capacitor between an energy storage mode which stores a charge in the capacitor, and an energy delivery mode, which conducts the charge to the stimulation electrode. In some embodiments, a pervoskite dielectric includes a mixture and BTO and other one or more materials, such as CCTO, to impart linear charging characteristics on the dielectric. In some embodiments, the pervoskite dielectric includes CCTO.

Embodiments of the present subject matter include connecting a capacitor to a circuit board. In some of these embodiments, the capacitor is inserted into a socket. In some of these embodiments, the socket is soldered to the circuit board. Some embodiments include flex circuitry to which a capacitor of the present subject matter is attached.

In various embodiments, the method includes disposing the capacitor in an implantable device housing such that the pervoskite dielectric is exposed to an interior surface of the implantable device housing.

Various embodiments include a method in which a capacitor is formed by a process including forming a first pervoskite layer. Some embodiments include forming a first electrode layer onto the first pervoskite layer. Embodiments of the present subject matter include forming a second pervoskite layer on the first electrode layer. Some embodiments include forming a second electrode layer onto the second pervoskite layer. Some embodiments additionally include forming a third pervoskite layer onto the second electrode layer and connecting the first and second electrode layers to the pulse control electronics. Some embodiments also include forming a pervoskite layer with chemical vapor deposition. In some embodiment, chemical vapor deposition includes pulsed vapor deposition.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

What is claimed is:

1. An apparatus, comprising:
an implantable device housing;
a circuit board disposed in the implantable device housing;
a capacitor fixed to the circuit board and disposed in the implantable device housing, the capacitor including a dielectric comprising $CaCu_3Ti_4O_{12}$, the dielectric insulating an anode from a cathode;
electronics adapted to charge the capacitor with a substantially linear increase in voltage over time with a constant applied charging current until a maximum voltage is reached;
pulse control electronics disposed in the implantable device housing and connected to the capacitor, wherein the capacitor comprises:
a first layer comprising $CaCu_3Ti_4O_{12}$;
a first electrode layer on the first layer;
a second layer comprising $CaCu_3Ti_4O_{12}$ on the first electrode layer; and
a second conductive electrode on the second layer comprising $CaCu_3Ti_4O_{12}$.

2. The apparatus of claim 1, wherein the capacitor has a volume of approximately 2.0 cubic centimeters.

3. The apparatus of claim 2, wherein the capacitor is adapted to store approximately 41 joules with the selected pulse voltage at approximately 800 volts.

4. The apparatus of claim 3, further comprising at least one stimulation electrode, with the pulse control electronics connecting the capacitor to the at least one stimulation electrode, the pulse control electronics adapted to discharge a charge stored in the capacitor to the stimulation electrode.

5. The apparatus of claim 4, wherein the capacitor includes a third pervoskite layer comprising $CaCu_3Ti_4O_{12}$ on the second conductive electrode.

6. The apparatus of claim 5, wherein the first layer is disposed on a substrate.

7. The apparatus of claim 6, further comprising an insulative carrier connected to the capacitor and at least partially enveloping the capacitor, the insulative carrier disposed between the implantable device housing and the capacitor.

8. The apparatus of claim 7, wherein the insulative carrier includes epoxy.

9. The apparatus of claim 7, wherein the insulative carrier includes a heat shrink film.

10. The apparatus of claim 7, wherein the insulative carrier includes epoxy.

11. The apparatus of claim 7, wherein the insulative carrier includes a rubber piece elastically deformed around the capacitor.

12. The apparatus of claim 7, wherein the insulative carrier includes a heat shrink film.

13. A method, comprising:
insulating an anode of a capacitor and a cathode of the capacitor with a dielectric comprising $CaCu_3Ti_4O_{12}$;
fixing the capacitor to a circuit board;
disposing the capacitor and the circuit board in an implantable device housing;
disposing pulse control electronics in the implantable device housing;
connecting the capacitor to a stimulation electrode and to the pulse control electronics, and
charging the capacitor with a constant current such that there is a substantially linear increase in voltage over time until a selected maximum voltage is reached,
wherein the pulse control electronics switch the capacitor between an energy storage mode which stores a charge in the capacitor, and an energy delivery mode, which conducts the charge to the stimulation electrode,
wherein the capacitor is formed by:
forming a first dielectric layer comprising $CaCu_3Ti_4O_{12}$;
forming a first electrode layer onto the first dielectric layer;
forming a second dielectric layer comprising $CaCu_3Ti_4O_{12}$ on the first electrode layer; and
forming a second electrode layer onto the second dielectric layer.

14. The method of claim 13, wherein the capacitor is formed by a process including,
forming a third dielectric layer comprising $CaCu_3Ti_4O_{12}$ onto the second electrode layer; and
connecting the first and second electrode layers to the pulse control electronics.

15. The method of claim 14, wherein chemical vapor deposition includes pulsed vapor deposition.

16. The method of claim 14, wherein the capacitor is formed by a process including mixing barium titanate with the $CaCu_3Ti_4O_{12}$ to form at least one of the group including the first dielectric layer, the second dielectric layer and the third dielectric layer.

17. The method of claim 16, wherein fixing the capacitor to the circuit board includes surface mounting the capacitor to the circuit board.

18. The method of claim 17, wherein fixing the capacitor to the circuit board includes coupling terminals of the capacitor to through holes of the circuit board.

19. The method of claim 18, wherein disposing the capacitor and the circuit board in an implantable device housing includes disposing the capacitor in the implantable device housing such that the dielectric is exposed to an interior surface of the implantable device housing.

20. The method of claim 13, wherein forming the first dielectric layer includes forming with chemical vapor deposition.

* * * * *